US009982021B2

(12) United States Patent
Heo et al.

(10) Patent No.: US 9,982,021 B2
(45) Date of Patent: May 29, 2018

(54) COMPOSITION FOR DISSOLVING THROMBI, AND A PHARMACEUTICAL COMPOSITION FOR TREATING STENOTIC OR OCCLUSIVE VASCULAR DISEASES WHICH COMPRISES THE SAME

(75) Inventors: Ji Hoe Heo, Seoul (KR); Il Kwon, Gyeonggi-do (KR); Young Dae Kim, Seoul (KR); Sung Yu Hong, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days. days.

(21) Appl. No.: 13/882,792

(22) PCT Filed: Nov. 1, 2011

(86) PCT No.: PCT/KR2011/008248
§ 371 (c)(1), (2), (4) Date: May 3, 2013

(87) PCT Pub. No.: WO2012/060607
PCT Pub. Date: May 10, 2012

(65) Prior Publication Data

US 2013/0316951 A1 Nov. 28, 2013

(30) Foreign Application Priority Data

Nov. 1, 2010 (KR) ........................ 10-2010-0107760

(51) Int. Cl.

| | |
|---|---|
| ***C07K 14/00*** | (2006.01) |
| ***C07K 7/06*** | (2006.01) |
| ***C07K 14/46*** | (2006.01) |
| ***A61K 38/06*** | (2006.01) |
| ***A61K 38/17*** | (2006.01) |
| ***C12N 9/64*** | (2006.01) |

(52) U.S. Cl.
CPC ............ *C07K 14/001* (2013.01); *A61K 38/06* (2013.01); *A61K 38/1703* (2013.01); *C07K 7/06* (2013.01); *C07K 14/46* (2013.01); *C12N 9/6489* (2013.01)

(58) Field of Classification Search
CPC ........ C07K 14/001; C07K 14/46; C07K 7/06; C07K 14/00; A61K 38/06; A61K 38/16; A61K 38/1703; A61K 38/4806
See application file for complete search history.

(56) References Cited

U.S. PATENT DOCUMENTS

| | | | |
|---|---|---|---|
| 5,498,601 A | 3/1996 | Sato et al. | |
| 7,033,788 B2 | 4/2006 | Chung et al. | |
| 2005/0032189 A1* | 2/2005 | Chung et al. | 435/226 |

FOREIGN PATENT DOCUMENTS

| | | |
|---|---|---|
| KR | 10-0458362 B1 | 11/2004 |
| KR | 10-0835736 B1 | 6/2008 |

OTHER PUBLICATIONS

J Musial, Inhibition of platelet adhesion to surfaces of extracorporeal circuits by disintegrins. RGD containing peptides from viper venoms. Circulation. 1990;82:261-273.*
UniProt Protein Database, Protein Accession Q9DGH6, Disintegrin Saxatilin, pp. 1-5, accessed on Aug. 5, 2014.*
Young-Doug Sohn, Acute and repeated dose toxicity studies of recombinant saxatilin, a disintegrin from the Korean snake, Toxicon 51 (2008) 406-417.*
Radke PW, Therapeutic dissolution of an intracoronary thrombus by prolonged intravenous platelet glycoprotein Ib/IIIa antagonism. J Invasive Cardiol, Nov. 1999; 11(11):679-681.*
Martin M. Bednar, Antiplatelet Therapy in Acute Cerebral Ischemia, Stroke, 1990;30:887-893.*
A. Pinto, Antiplatelet treatment in ischemic stroke treatment, Curr Top Med Chem. 2009;9(14):1298316.*
International Search Report for PCT/KR2011/008248.
Edwin A. Clark, et al. "Structurally Distinct Disintegrins Contortrostatin and Multiisquamatin Differentially Regulate Platelet Tyrosine Phosphorylation" J. Biol. Chern., vol. 269(35), pp. 21940-21943 (1994) See p. 21940.

* cited by examiner

*Primary Examiner* — James H Alstrum-Acevedo
*Assistant Examiner* — Erinne R Dabkowski
(74) *Attorney, Agent, or Firm* — Harness, Dickey & Pierce, P.L.C.

(57) ABSTRACT

The present invention relates to: a composition for dissolving thrombi comprising a peptide comprising the Arg-Gly-Asp motif; a pharmaceutical composition for treating stenotic or occlusive vascular diseases which comprises the same; and a thrombus dissolving method and a method for treating stenotic or occlusive vascular diseases, comprising the step of administering the same. The compositions and methods of the present invention have the advantage that they effectively break down already formed thrombi by adopting the principle of targeting integrin within the thrombus such as platelet surface GPIIb-IIIa, which is not the same as the existing principle of plasminogen activation. Also, the compositions and methods of the present invention have a nerve-protecting function as they effectively open as far as the microvasculature, without the occurrence of restenosis after penetration.

3 Claims, 9 Drawing Sheets

SEQUENCE LISTING

```
<160> NUMBER OF SEQ ID NOS: 21

<210> SEQ ID NO 1
<211> LENGTH: 6
<212> TYPE: PRT
<213> ORGANISM: Artificial Sequence
<220> FEATURE:
<223> OTHER INFORMATION: aritificially made peptide comprising
      Arg-Gly-Asp motif having thrombolytic activity

<400> SEQUENCE: 1

Gly Arg Gly Asp Ser Pro
1               5


<210> SEQ ID NO 2
<211> LENGTH: 10
<212> TYPE: PRT
<213> ORGANISM: Artificial Sequence
<220> FEATURE:
<223> OTHER INFORMATION: aritificially made peptide comprising
      Arg-Gly-Asp motif having thrombolytic activity

<400> SEQUENCE: 2

Gly Ser Ser Gly Arg Gly Asp Ser Pro Ala
1               5                   10


<210> SEQ ID NO 3
<211> LENGTH: 57
<212> TYPE: PRT
<213> ORGANISM: Artificial Sequence
<220> FEATURE:
<223> OTHER INFORMATION: aritificially made peptide comprising
      Arg-Gly-Asp motif having thrombolytic activity

<400> SEQUENCE: 3

Asp Ala Ala Thr Cys Lys Leu Arg Pro Gly Ala Gln Cys Ala Glu Gly
1               5                   10                  15

Leu Cys Cys Asp Gln Cys Arg Phe Met Lys Glu Gly Thr Ile Cys Arg
            20                  25                  30

Met Ala Arg Gly Asp Asp Met Asp Asp Tyr Cys Asn Gly Ile Ser Ala
        35                  40                  45

Gly Cys Pro Arg Asn Pro Phe His Ala
    50                  55


<210> SEQ ID NO 4
<211> LENGTH: 56
<212> TYPE: PRT
```

<213> ORGANISM: Artificial Sequence
<220> FEATURE:
<223> OTHER INFORMATION: aritificially made peptide comprising
Arg-Gly-Asp motif having thrombolytic activity

<400> SEQUENCE: 4

```
Ala Ala Thr Cys Lys Leu Arg Pro Gly Ala Gln Cys Ala Glu Gly Leu
1               5                   10                  15

Cys Cys Asp Gln Cys Arg Phe Met Lys Glu Gly Thr Ile Cys Arg Met
            20                  25                  30

Ala Arg Gly Asp Asp Met Asp Asp Tyr Cys Asn Gly Ile Ser Ala Gly
        35                  40                  45

Cys Pro Arg Asn Pro Phe His Ala
    50                  55
```

<210> SEQ ID NO 5
<211> LENGTH: 55
<212> TYPE: PRT
<213> ORGANISM: Artificial Sequence
<220> FEATURE:
<223> OTHER INFORMATION: aritificially made peptide comprising
Arg-Gly-Asp motif having thrombolytic activity

<400> SEQUENCE: 5

```
Ala Thr Cys Lys Leu Arg Pro Gly Ala Gln Cys Ala Glu Gly Leu Cys
1               5                   10                  15

Cys Asp Gln Cys Arg Phe Met Lys Glu Gly Thr Ile Cys Arg Met Ala
            20                  25                  30

Arg Gly Asp Asp Met Asp Asp Tyr Cys Asn Gly Ile Ser Ala Gly Cys
        35                  40                  45

Pro Arg Asn Pro Phe His Ala
    50                  55
```

<210> SEQ ID NO 6
<211> LENGTH: 53
<212> TYPE: PRT
<213> ORGANISM: Artificial Sequence
<220> FEATURE:
<223> OTHER INFORMATION: aritificially made peptide comprising
Arg-Gly-Asp motif having thrombolytic activity

<400> SEQUENCE: 6

```
Cys Lys Leu Arg Pro Gly Ala Gln Cys Ala Glu Gly Leu Cys Cys Asp
1               5                   10                  15

Gln Cys Arg Phe Met Lys Glu Gly Thr Ile Cys Arg Met Ala Arg Gly
            20                  25                  30

Asp Asp Met Asp Asp Tyr Cys Asn Gly Ile Ser Ala Gly Cys Pro Arg
        35                  40                  45

Asn Pro Phe His Ala
    50
```

<210> SEQ ID NO 7
<211> LENGTH: 46
<212> TYPE: PRT
<213> ORGANISM: Artificial Sequence
<220> FEATURE:
<223> OTHER INFORMATION: aritificially made peptide comprising
Arg-Gly-Asp motif having thrombolytic activity

<400> SEQUENCE: 7

```
Cys Lys Leu Arg Pro Gly Ala Gln Cys Ala Glu Gly Leu Cys Cys Asp
1               5                   10                  15
```

-continued

```
Gln Cys Arg Phe Met Lys Glu Gly Thr Ile Cys Arg Met Ala Arg Gly
            20                  25                  30

Asp Asp Met Asp Asp Tyr Cys Asn Gly Ile Ser Ala Gly Cys
        35                  40                  45


<210> SEQ ID NO 8
<211> LENGTH: 54
<212> TYPE: PRT
<213> ORGANISM: Artificial Sequence
<220> FEATURE:
<223> OTHER INFORMATION: aritificially made peptide comprising
      Arg-Gly-Asp motif having thrombolytic activity

<400> SEQUENCE: 8

Asp Ala Ala Thr Cys Lys Leu Arg Pro Gly Ala Gln Cys Ala Glu Gly
1               5                   10                  15

Leu Cys Cys Asp Gln Cys Arg Phe Met Lys Glu Gly Thr Ile Cys Arg
            20                  25                  30

Met Ala Arg Gly Asp Asp Met Asp Asp Tyr Cys Asn Gly Ile Ser Ala
        35                  40                  45

Gly Cys Pro Arg Asn Pro
    50


<210> SEQ ID NO 9
<211> LENGTH: 53
<212> TYPE: PRT
<213> ORGANISM: Artificial Sequence
<220> FEATURE:
<223> OTHER INFORMATION: aritificially made peptide comprising
      Arg-Gly-Asp motif having thrombolytic activity

<400> SEQUENCE: 9

Ala Ala Thr Cys Lys Leu Arg Pro Gly Ala Gln Cys Ala Glu Gly Leu
1               5                   10                  15

Cys Cys Asp Gln Cys Arg Phe Met Lys Glu Gly Thr Ile Cys Arg Met
            20                  25                  30

Ala Arg Gly Asp Asp Met Asp Asp Tyr Cys Asn Gly Ile Ser Ala Gly
        35                  40                  45

Cys Pro Arg Asn Pro
    50


<210> SEQ ID NO 10
<211> LENGTH: 52
<212> TYPE: PRT
<213> ORGANISM: Artificial Sequence
<220> FEATURE:
<223> OTHER INFORMATION: aritificially made peptide comprising
      Arg-Gly-Asp motif having thrombolytic activity

<400> SEQUENCE: 10

Ala Thr Cys Lys Leu Arg Pro Gly Ala Gln Cys Ala Glu Gly Leu Cys
1               5                   10                  15

Cys Asp Gln Cys Arg Phe Met Lys Glu Gly Thr Ile Cys Arg Met Ala
            20                  25                  30

Arg Gly Asp Asp Met Asp Asp Tyr Cys Asn Gly Ile Ser Ala Gly Cys
        35                  40                  45

Pro Arg Asn Pro
    50


<210> SEQ ID NO 11
<211> LENGTH: 50
<212> TYPE: PRT
```

-continued

<213> ORGANISM: Artificial Sequence
<220> FEATURE:
<223> OTHER INFORMATION: aritificially made peptide comprising
      Arg-Gly-Asp motif having thrombolytic activity

<400> SEQUENCE: 11

```
Cys Lys Leu Arg Pro Gly Ala Gln Cys Ala Glu Gly Leu Cys Cys Asp
1               5                   10                  15

Gln Cys Arg Phe Met Lys Glu Gly Thr Ile Cys Arg Met Ala Arg Gly
            20                  25                  30

Asp Asp Met Asp Asp Tyr Cys Asn Gly Ile Ser Ala Gly Cys Pro Arg
        35                  40                  45

Asn Pro
    50
```

<210> SEQ ID NO 12
<211> LENGTH: 73
<212> TYPE: PRT
<213> ORGANISM: Agkistrodon saxatilis emelianov

<400> SEQUENCE: 12

```
Glu Ala Gly Glu Glu Cys Asp Cys Gly Ala Pro Ala Asn Pro Cys Cys
1               5                   10                  15

Asp Ala Ala Thr Cys Lys Leu Arg Pro Gly Ala Gln Cys Ala Glu Gly
            20                  25                  30

Leu Cys Cys Asp Gln Cys Arg Phe Met Lys Glu Gly Thr Ile Cys Arg
        35                  40                  45

Met Ala Arg Gly Asp Asp Met Asp Asp Tyr Cys Asn Gly Ile Ser Ala
    50                  55                  60

Gly Cys Pro Arg Asn Pro Phe His Ala
65                  70
```

<210> SEQ ID NO 13
<211> LENGTH: 177
<212> TYPE: DNA
<213> ORGANISM: Artificial Sequence
<220> FEATURE:
<223> OTHER INFORMATION: SX-1 (converted from the saxatilin gene while
      codon optimization with codon usage frequency was undertaken for
      expression of the saxatilin gene in Pichia host cells)

<400> SEQUENCE: 13

```
gatgctgcaa cctgtaaact gagaccaggg gcgcagtgtg cagaaggact gtgttgtgac      60

cagtgcagat ttatgaaaga aggaacaata tgccggatgg caaggggtga tgacatggat     120

gattactgca atggcatatc tgctggctgt cccagaaatc ccttccatgc ctaataa        177
```

<210> SEQ ID NO 14
<211> LENGTH: 174
<212> TYPE: DNA
<213> ORGANISM: Artificial Sequence
<220> FEATURE:
<223> OTHER INFORMATION: SX-2 (converted from the saxatilin gene while
      codon optimization with codon usage frequency was undertaken for
      expression of the saxatilin gene in Pichia host cells)

<400> SEQUENCE: 14

```
gctgcaacct gtaaactgag accaggggcg cagtgtgcag aaggactgtg ttgtgaccag      60

tgcagattta tgaaagaagg aacaatatgc cggatggcaa ggggtgatga catggatgat     120

tactgcaatg gcatatctgc tggctgtccc agaaatccct tccatgccta ataa           174
```

-continued

```
<210> SEQ ID NO 15
<211> LENGTH: 171
<212> TYPE: DNA
<213> ORGANISM: Artificial Sequence
<220> FEATURE:
<223> OTHER INFORMATION: SX-3 (converted from the saxatilin gene while
      codon optimization with codon usage frequency was undertaken for
      expression of the saxatilin gene in Pichia host cells)

<400> SEQUENCE: 15

gcaacctgta aactgagacc aggggcgcag tgtgcagaag gactgtgttg tgaccagtgc      60

agatttatga aagaaggaac aatatgccgg atggcaaggg gtgatgacat ggatgattac     120

tgcaatggca tatctgctgg ctgtcccaga aatcccttcc atgcctaata a              171


<210> SEQ ID NO 16
<211> LENGTH: 165
<212> TYPE: DNA
<213> ORGANISM: Artificial Sequence
<220> FEATURE:
<223> OTHER INFORMATION: XL-1 (converted from the saxatilin gene while
      codon optimization with codon usage frequency was undertaken for
      expression of the saxatilin gene in Pichia host cells)

<400> SEQUENCE: 16

tgtaaactga gaccaggggc gcagtgtgca gaaggactgt gttgtgacca gtgcagattt      60

atgaaagaag gaacaatatg ccggatggca aggggtgatg acatggatga ttactgcaat     120

ggcatatctg ctggctgtcc cagaaatccc ttccatgcct aataa                     165


<210> SEQ ID NO 17
<211> LENGTH: 144
<212> TYPE: DNA
<213> ORGANISM: Artificial Sequence
<220> FEATURE:
<223> OTHER INFORMATION: XL-2 (converted from the saxatilin gene while
      codon optimization with codon usage frequency was undertaken for
      expression of the saxatilin gene in Pichia host cells)

<400> SEQUENCE: 17

tgtaaactga gaccaggggc gcagtgtgca gaaggactgt gttgtgacca gtgcagattt      60

atgaaagaag gaacaatatg ccggatggca aggggtgatg acatggatga ttactgcaat     120

ggcatatctg ctggctgtta ataa                                            144


<210> SEQ ID NO 18
<211> LENGTH: 156
<212> TYPE: DNA
<213> ORGANISM: Artificial Sequence
<220> FEATURE:
<223> OTHER INFORMATION: XL-3 (converted from the saxatilin gene while
      codon optimization with codon usage frequency was undertaken for
      expression of the saxatilin gene in Pichia host cells)

<400> SEQUENCE: 18

tgtaaactga gaccaggggc gcagtgtgca gaaggactgt gttgtgacca gtgcagattt      60

atgaaagaag gaacaatatg ccggatggca aggggtgatg acatggatga ttactgcaat     120

ggcatatctg ctggctgtcc cagaaatccc taataa                               156


<210> SEQ ID NO 19
<211> LENGTH: 168
<212> TYPE: DNA
<213> ORGANISM: Artificial Sequence
<220> FEATURE:
<223> OTHER INFORMATION: LS-1 (converted from the saxatilin gene while
      codon optimization with codon usage frequency was undertaken for
```

-continued

```
      expression of the saxatilin gene in Pichia host cells)

<400> SEQUENCE: 19

gatgctgcaa cctgtaaact gagaccaggg gcgcagtgtg cagaaggact gtgttgtgac      60

cagtgcagat ttatgaaaga aggaacaata tgccggatgg caaggggtga tgacatggat     120

gattactgca atggcatatc tgctggctgt cccagaaatc cctaataa                  168


<210> SEQ ID NO 20
<211> LENGTH: 165
<212> TYPE: DNA
<213> ORGANISM: Artificial Sequence
<220> FEATURE:
<223> OTHER INFORMATION: LS-2 (converted from the saxatilin gene while
      codon optimization with codon usage frequency was undertaken for
      expression of the saxatilin gene in Pichia host cells)

<400> SEQUENCE: 20

gctgcaacct gtaaactgag accaggggcg cagtgtgcag aaggactgtg ttgtgaccag      60

tgcagattta tgaaagaagg aacaatatgc cggatggcaa ggggtgatga catggatgat     120

tactgcaatg gcatatctgc tggctgtccc agaaatccct aataa                     165


<210> SEQ ID NO 21
<211> LENGTH: 162
<212> TYPE: DNA
<213> ORGANISM: Artificial Sequence
<220> FEATURE:
<223> OTHER INFORMATION: LS-3 (converted from the saxatilin gene while
      codon optimization with codon usage frequency was undertaken for
      expression of the saxatilin gene in Pichia host cells)

<400> SEQUENCE: 21

gcaacctgta aactgagacc aggggcgcag tgtgcagaag gactgtgttg tgaccagtgc      60

agatttatga aagaaggaac aatatgccgg atggcaaggg gtgatgacat ggatgattac     120

tgcaatggca tatctgctgg ctgtcccaga aatccctaat aa                        162
```

COMPOSITION FOR DISSOLVING THROMBI, AND A PHARMACEUTICAL COMPOSITION FOR TREATING STENOTIC OR OCCLUSIVE VASCULAR DISEASES WHICH COMPRISES THE SAME

CROSS REFERENCE TO RELATED APPLICATIONS AND CLAIM OF PRIORITY

This patent application is a National Phase application under 35 U.S.C. § 371 of International Application No. PCT/KR2011/008248, filed on Nov. 1, 2011, which claims priority to Korean Patent Application number 10-2010-0107760, filed Nov. 1, 2010, entire contents of which are incorporated herein by reference.

FIELD OF THE INVENTION

The present invention relates to a composition for dissolving thrombus and a pharmaceutical composition for treating stenotic or occlusive vascular diseases comprising the same.

DESCRIPTION OF THE RELATED ART

The majority of strokes is caused by thromboembolic occlusion of major or smaller intracerebral arteries (Wardlaw, Murray et al. 2009). In ischemic stroke, rapid thrombolysis is the only established therapeutic option to prevent development of inescapable complete infarction (1995; Choi, Bateman et al. 2006). Treatment by intravenous administration of recombinant tissue plasminogen activator (r-tPA) is the first and currently the only approved therapy for ischemic stroke within 3 hours of symptom onset (Caplan, Mohr et al. 1997; Lopez-Yunez, Bruno et al. 2001). However, more than half patients fail to achieve successful recanalization after thrombolytic treatment (Rha and Saver 2007)[Lee et al. Stroke 2007; 38:192-193]. Even if an occluded artery is recanalized successfully by the thrombolytic treatment, its benefits are deducted by the risks of reperfusion injury (Hallenbeck and Dutka 1990), intracerebral hemorrhage (Adams, Adams et al. 2005), and reocclusion (Heo, Lee et al 2003). rt-PA was also suggested to have neurotoxicity (Chen and Strickland 1997; Wang, Tsirka et al. 1998; Nicole, Docagne et al. 2001; Yepes, Sandkvist et al. 2002; Matys and Strickland 2003).

As the recanalization strategy has proven efficacy, but had limited potency and potential adverse effects, there have been efforts to develop new thrombolytic agents with better effects than it-PA. They include variants of t-PA, plasminogen activators from animal sources, and microplasmin. These drugs aimed at as follows: (a) enhancing fibrin specificity; (2) extending plasma half life; (3) being less inhibited by plasminogen activator inhibitor-1; and (d) avoiding neurotoxicity. Several drugs completed clinical trials and some are on studying their efficacy. These drugs target fibrin of the thrombus. However, the thrombus is formed by platelet-fibrinogen interaction. Thrombin, leukocytes and red blood cells are also components of the thrombus. Resistance of the thrombi to thrombolytic agents targeting the fibrin is one of main reasons of low recanalization rates in stroke patients, which may occur more common in occlusion by platelet-rich thrombi. In this regard, treatment targeting platelets may be an alternative or additive to treatment targeting fibrin for improved thrombolytic efficacy.

Platelet glycoprotein (GP) IIb/IIIa, a member of integrin family, exists on the surface of platelet membrane with high density (Shattil and Ginsberg 1997). The GPIIb/IIIa receptor mediates the final common pathway of platelet aggregation by specific binding to fibrinogen (Phillips, Charo et al. 1988). Therefore, targeting the platelet GPIIb/IIIa receptor has been the mainstay for the drug development acting against the platelets. Several platelet GPIIb/IIIa antagonists have been developed, which include the Fab fragment of a human-mouse chimeric antibody against GP IIb/IIIa (abciximab), nonpeptide analogues of an RGD peptide (tirofiban and lamifiban), and a cyclic heptapeptide disintegrin containing KGD motif (eptifibatide) (Seitz, Meisel et al. 2004; Abou-Chebl, Bajzer et al 2005; Eckert, Koch et al. 2005). These GPIIb/IIIa antagonists have been effective in patients with unstable angina, acute myocardial infarction and percutaneous transfemoral coronary angioplasty and stent. In stroke, abciximab failed to show efficacy in patients who were treated 5 to 6 hours after the symptom onset (Adams, Effron et al. 2008). However, GPIIb/IIIa antagonists resolve the thrombi in stroke patients with reocclusion and are effective in selected patients (Heo, Lee et al. 2003; Seitz, Hamzavi et al. 2003; Seitz, Meisel et al. 2004; Eckert, Koch et al. 2005; Chen, Mo. et al. 2007). In addition, GPIIb/IIIa inhibitors are beneficial to preserve microvascular patency in animal stroke and may have neuroprotective effect (Choudhri, Hoh et al. 1998; Abumiya, Fitridge et al. 2000).

Saxatilin, a novel disintegrin purified and cloned from Korean snake (Gloydius saxatilis) venom has the tripeptide sequence Arg-Gly-Asp (RGD), which is a recognition site of disintegrins to a platelet GPIIb/IIIa receptor (Hong, Koh et al. 2002; Hong, Sohn et al. 2002). Saxatilin has strong inhibitory effects on platelet aggregation (Hong, Koh et al. 2002) and platelet activation (Jang, Jeon et al. 2007) such that thrombus formation is interrupted.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY

The present inventors have made intensive researches to develop a thrombolytic agent for treating stenotic or occlusive vascular diseases by dissolving preformed thrombus. As a result, they have found that a peptide comprising Arg-Gly-Asp motif has excellent thrombolytic activity to preformed thrombus in the blood vessel.

Accordingly, it is an object of this invention to provide a composition for thrombolysis.

It is another object of this invention to provide a pharmaceutical composition for treating stenotic or occlusive vascular diseases comprising the same.

Other objects and advantages of the present invention will become apparent from the detailed description to follow taken in conjugation with the appended claims and drawings.

In one aspect of the present invention, there is provided a composition for thrombolysis, comprising (a) a therapeutically effective amount of a peptide comprising Arg-Gly-Asp motif; and (b) a pharmaceutically acceptable carrier.

Tripeptide sequence Arg-Gly-Asp (RGD) is recognition site of disintegrin (Hong, Koh et al, 2002; Hong Sohn et al, 2002). Disintegrin is a representative example including a peptide including Arg-Gly-Asp motif. It has been already known that disintegrin inhibits platelet aggregation to interrupt thrombus formation. However, there is not known whether disintegrin has thrombolytic activity to preformed thrombus in vivo. The present inventors have found that a peptide comprising Arg-Gly-Asp motif has excellent thrombolytic activity to preformed thrombus in the blood vessel.

The term used herein "a peptide comprising Arg-Gly-Asp motif" encompasses to amino acid-based molecule which dissolves thrombus by binding to integrin present in thrombus. It may be used as long as amino acid-based molecule includes Arg-Gly-Asp motif as recognition site of disintegrin, but not limited to, length, modification and electrical Property of peptide.

The peptide comprising Arg-Gly-Asp motif used as an active ingredient of the present composition for thrombolysis binds to integrin present in thrombus to dissolve thrombus by principle of competition binding, preferably GP (glycoprotein) IIb/IIIa present on the surface of platelet forming thrombus.

According to an embodiment, the peptide comprising Arg-Gly-Asp motif of the present invention is a peptide comprising the amino acid sequence selected from a group consisting of the amino acid sequences as set forth in SEQ ID NOs:1-11.

According to another embodiment, the peptide comprising Arg-Gly-Asp motif of the present invention is a peptide consisted of the amino acid sequence selected from a group consisting of the amino acid sequences as set forth in SEQ ID NOs:1-11

According to still another embodiment, the peptide comprising Arg-Gly-Asp motif of the present invention is disintegrin. For example, the disintegrin includes, but not limited to, saxatilin, rhodostomin, albolabrin, applagin, basilicin, batroxostatin, bitistatin, barbourin, cereberin, cerastin, crotatroxin, durissin, echistatin, elegantin, eristicophin, flavoridin, flavostatin, halysin, jararacin, jarastatin, jararin, lachesin, lutosin, molossin, salmosin, tergeminin, trigramin, trimestatin, trimucrin, trimutase, ussuristatin and viridin.

According to still another embodiment, the peptide comprising Arg-Gly-Asp motif is saxatilin, preferably the saxatilin comprises the amino acid sequence as set forth in SEQ ID NO:12.

In addition to this, the peptide comprising Arg-Gly-Asp motif of the present invention having thrombolytic activity is preferably oligonucleotide (GRGDSP) represented by SEQ ID NO:1 and its cyclic GRGDSP, and oligonucleotide represented by the amino acid sequence selected from a group consisting of the amino acid sequences as set forth in SEQ ID NOs:2-11, but not limited thereto.

The peptide comprising Arg-Gly-Asp motif as an active ingredient for thrombolysis of the present composition may be used with thrombolytic agents known in the art, such as plasminogen activator. Furthermore, without thrombolytic agents known in the art, it may be used alone to effectively dissolve thrombus, which is already generated, and there is no reocclusion or side effects such as bleeding.

According to an embodiment, the present composition for thrombolysis comprises no plasminogen activator.

According to another embodiment, the thrombolytic active ingredient of the present composition for thrombolysis consists of the peptide comprising Arg-Gly-Asp motif.

The present composition for thrombolysis may further include a pharmaceutically acceptable carrier.

The pharmaceutically acceptable carrier included in the composition of the present invention includes, as one generally used at the time of preparing, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxylbenzoate, propyl hydroxy benzoate, propyl hydroxy benzoate, talc, stearic acid, magnesium and mineral oil, but the present invention is not limited thereto. The pharmaceutical composition of the present invention may further include a lubricant, a wetting agent, a sweetening agent, emulsion, suspension, preservatives, and the like. The suitable pharmaceutically acceptable carrier or formulations are described in detail in *Remington's Pharmaceutical Sciences* (19th ed., 1995).

In another aspect of the present invention, there is provided a pharmaceutical composition for treating stenotic or occlusive vascular diseases which comprises the composition for thrombolysis.

Since the present pharmaceutical composition is the pharmaceutical composition which may treat subject diseases by dissolving thrombus using the composition for thrombolysis as described above, the common descriptions between them are omitted in order to avoid undue redundancy leading to the complexity of this Specification.

The present pharmaceutical composition has an important feature that it may be effectively dissolved thrombus, which has been already generated and aggregated, to treat various stenotic or occlusive vascular diseases. i.e., the present pharmaceutical composition not only prevents thrombus generation to treat stenotic or occlusive vascular diseases, but also dissolves thrombus which has been already generated to treat thereof.

The term used herein "occlusion" encompasses to states that the blood vessel is completely blocked or narrowed by partially blocking. The level of occlusion mentioned in the present invention may be determined on the basis of the measured blood flow. i.e., the level of occlusion is classified as partial occlusion or complete occlusion. Partial occlusion means that the blood flow is reduced to the level of 50-60% of normal blood flow (baseline blood flow), and complete occlusion means that the blood flow is reduced to the level of 90-100% of that (see: FIG. 2).

The present pharmaceutical composition may further include a pharmaceutically acceptable carrier. The pharmaceutically acceptable carrier is described as above.

The present pharmaceutical composition may be administered by intravenous injection, intra-arterial injection, local injection, intraventricular injection, intrathecal injection, subcutaneous injection, intraperitoneal injection and transdermal injection, preferably manner which is injected directly into the blood vessel. The manner which is injected directly into the blood vessel means the injection into the blood vessel including artery, vein and capillary, for example, aorta, carotid, subclavian artery, celiac artery, mesenteric arteries, renal arteries, iliac arteries, arterioles, capillaries, veinlets. The administration method may be selected appropriately according to the blood vessel portion in which thrombus generates.

A proper dosage of the pharmaceutical composition according to the present invention may be variously prescribed according to factors such as a formulation method, an administration method, age of a patient, body weight of a patient, sex of a patient, a pathosis of a patient, food, an administration period, an administration route, an excretion rate, and reaction sensitivity. The ordinarily skilled physician may easily decide and prescribe to the effective dose for the treatment desired. A dosage included in the pharmaceutical composition of the present invention is within a range of 0.001 to 100 mg/kg, preferably 0.001 to 1000 mg/kg based on an adult.

The pharmaceutical composition of the present invention may be prepared in a type of unit capacity or by putting in high capacity container through preparing with a pharmaceutically acceptable carrier and/or excipient according to the method that can be easily performed by a person skilled in the art relating to the present invention. At this time, the dosage form may be a type of solution, suspension, syrups, or emulsion in an oil or aqueous medium, or may be a type of extracts, discutient, powders, granulars, tablets, or capsules. In addition, it may further include a dispersant or a stabilizer.

The peptide comprising Arg-Gly-Asp motif as an active ingredient for thrombolysis of the present pharmaceutical composition may be used with thrombolytic agents known in the art, such as plasminogen activator. Furthermore, without thrombolytic agents known in the art, it may be used alone to effectively dissolve thrombus, which is already generated, and there is no reocclusion or side effects such as bleeding.

According to an embodiment, the present pharmaceutical composition for thrombolysis comprises no plasminogen activator.

According to another embodiment, the thrombolytic active ingredient of the present pharmaceutical composition for thrombolysis consists of the peptide comprising Arg-Gly-Asp motif.

Diseases which may be treated by the present pharmaceutical composition include a variety of vascular stenosis or occlusive disease, for instance, cerebrovascular disease (CVD), cardiovascular disease, arteriovascular disease, coronary artery disease (CAD), peripheral artery disease (PAD), preferably stroke, cerebral infarction, cerebral thrombosis, cerebral embolism, acunar infarction, acute coronary syndrome, angina pectoris, coarctation of aorta, myocardial infarction, migraine, bundle branch block, cerebral ischemia, acute ischemic arteriovascular event, thrombophlebitis, venousthromboembolism, deep vein thrombosis, pulmonary embolism, peripheral vascular disease, vascular headache, atherosclerosis, vascular spasm, restenosis, restenosis after balloon angioplast and occlusion of vessel by vasculitis, and most preferably stroke, cerebral infarction, cerebral thrombosis, cerebral embolism, myocardial infarction.

The term used herein "cerebrovascular disease (CVD)" refers to arteriosclerotic vessel disease occurring in blood vessel which supply the oxygen-rich blood to face and brain. In general, it includes ischemic disease as well as comorbid disease CAD and/or PAD (peripheral artery disease). For example, CVD includes ischemic cerebrovascular disease, acute ischemic stroke, ischemic stroke, hemorrhagic stroke, varicose veins, mild cognitive impairment (MCI) or transient ischemic attacks (TIA), but is not limited thereto.

The term used herein "cardiovascular disease" or "arteriosclerotic vascular disease" is general term used in classifying numerous states affecting the heart, heart valves, blood and vasculature. It includes diseases affecting the heart or blood vessels, preferably the metabolic syndrome, syndrome X, atherosclerosis, thrombosis, atherosclerosis, coronary artery disease, stable and unstable angina, stroke, aortic stenosis or aortic aneurysm disease, cerebrovascular disease, peripheral vascular disease or acute ischemic atherosclerotic events, but is not limited thereto. In general, the term used herein "arteriosclerotic vascular disease" means ischemic diseases or proischemic diseases rather than non-ischemic diseases.

The term used herein "coronary artery disease (CAD)" means arteriosclerotic vessel disease that artery (coronary artery) supplying blood to the heart muscle is hardened and/or narrowed by atherosclerotic or precipitation of calcium to occur. CAD results in reduction of the blood flow to the heart muscle such that the heart muscle is starved for a sufficient amount of oxygen to cause necrosis. CAD includes acute coronary artery syndrome, myocardial infarction (heart attack), angina (stable and unstable), atherosclerosis and atherothrombosis, but is not limited thereto.

The term used herein "peripheral artery disease (PAD)" refers to diseases of any of the blood vessels outside of the heart and brain. In general, it includes comorbid disease occurred with CAD.

The present pharmaceutical composition has an important feature that it may be effectively dissolved thrombus, which has been already generated and aggregated, to treat various stenotic or occlusive vascular diseases.

For example, in the case of cerebral infarction, pharmaceutical compositions for preventing thrombus generation have been already well-known (e.g., aspirin). However, once cerebral infarction is occurred by thrombus generation and brain blood vessel occlusion, there are no pharmaceutical compositions which may effectively treat it.

Treatment by intravenous administration of recombinant tissue plasminogen activator (r-tPA) is currently the only approved therapy for cerebral infarction within 3 hours of symptom onset. However, more than half patients fail to achieve successful recanalization after thrombolytic treatment. Under such circumstances, the present pharmaceutical composition, which may effectively dissolve preformed thrombus, is a realistic and groundbreaking approach in treatment of stenotic or occlusive vascular diseases already occurred. In addition, the present pharmaceutical composition for treating stenotic or occlusive vascular diseases possesses great value in terms of that it effectively treats the occlusion of microvessel and also restenosis does not occur.

In still another aspect of the present invention, there is provided a peptide having thrombolytic activity, which consists of any one of the amino acid sequence selected from a group consisting of the amino acid sequences as set forth in SEQ ID NOs:3-11.

In further aspect of the present invention, there is provided a method for thrombolysis, comprising administering to a blood vessel a peptide comprising Arg-Gly-Asp motif.

In still further aspect of the present invention, there is provided a method for treating stenotic or occlusive vascular diseases, comprising administering to a blood vessel a peptide comprising Arg-Gly-Asp motif.

Since the present methods for thrombolysis and treating stenotic or occlusive vascular diseases are methods which dissolve thrombus using the peptide as described above, the common descriptions between them are omitted in order to avoid undue redundancy leading to the complexity of this Specification.

The present peptide is saxatilin derivatives (i.e., deletion mutants) based on the amino acid sequence of saxatilin (SEQ ID NO:12), which is prepared with optimized amino acid sequences by predicting sequences exhibiting more effective saxatilin activity, i.e., ability to thrombolysis to preformed thrombus.

The present saxatilin derivatives have excellent pharmaceutical property than full-length saxatilin.

First, the present saxatilin derivatives length is shorter than full-length wild type saxatilin. However, its ability for thrombolysis is similar (see: FIGS. 7 and 8).

Second, since the immunogenicity of the present saxatilin derivatives is reduced to induce immune response to the extent less than the full-length wild type saxatilin, it has excellent safety as compared with the full-length wild type saxatilin.

Third, the present saxatilin derivatives show the tendency that post-recanalization reocclusion frequency and the blood flow fluctuation were significantly reduced in thrombolytic treatment by saxatilin derivatives (SX1) compared with the wild type saxatilin, addressing that the normal blood flow was stably maintained (see: FIGS. 7 and 8). Such thrombolytic pattern of saxatilin derivatives results in increase of therapeutic efficacy and reduction of side effects as compared to wild type saxatilin.

The term used herein "peptide" refers to a linear molecule formed by linking amino acid residues through peptide bonds.

The peptides of the present invention may be prepared by conventional chemical synthesis processes known to one of skill in the art, in particular, solid-phase synthesis techniques (Merrifield, *J. Amer. Chem. Soc.* 85:2149-54 (1963); Stewart, et al., *Solid Phase Peptide Synthesis,* 2nd. ed., Pierce Chem. Co.: Rockford, 111 (1984)).

Even though the peptide of this invention per se has higher stability than natural-occurring saxatilin, modifications of amino acid enable to have much higher stability. According to a preferred embodiment, C-terminal of the peptide may be modified to —OH or —$NH_2$, N-terminal of the peptide may be combined with a protection group selected from the group consisting of acetyl group, fluorenyl methoxy carbonyl group, formyl group, palmitoyl group, myristyl group, stearyl group, polyethylene glycol (PEG) and an amino acid.

The modifications of amino acid as described above are also responsible for the stability of the present peptides. The term used herein "stability" refers to in vivo stability and storage stability (e.g., storage stability at room temperature) as well. The protection group as described above protects the peptides from the attack of protease in vivo.

According to a preferred embodiment, the peptide comprising Arg-Gly-Asp motif of the present invention includes SX1 (SEQ ID NO:3), SX2 (SEQ ID NO:4), SX3 (SEQ ID NO:5), XL1 (SEQ ID NO:6), XL2 (SEQ ID NO:7), XL3 (SEQ ID NO:11), LS1 (SEQ ID NO:8), LS2 (SEQ ID NO:9) and LS3 (SEQ ID NO:10), more preferably SX1, SX2, SX3 and XL2, still more preferably SX1 and SX3, most preferably SX1.

According to the present invention, the method of the present invention may be effectively applied in the treatment of blood vessels by thrombus formed. In other words, the peptide comprising Arg-Gly-Asp motif of the present invention may not only inhibit the formation of thrombus, but also effectively dissolve preformed thrombus. Therefore, the present method may be effectively applied to patient (e.g., cerebral infarction) occurred vascular occlusion (partial or complete occlusion) by dissolving preformed thrombus to treat.

According to the present invention, treatment concentration of the peptide comprising Arg-Gly-Asp motif in the present invention is 1-100 mg/kg, more preferably 5-70 mg/kg, most preferably 10-40 mg/kg.

According to the present invention, the method of the present invention may be applied to animal. The animal is not particularly limited and includes preferably mammals, more preferably humans, mouse, rat, rabbit, monkey, pig, horse, cattle, sheep, antelope, dog or cat, still more preferably human or mouse.

According to the present invention, the animal vessel includes artery, vein and capillary, more preferably aorta, carotid, subclavian artery, celiac artery, mesenteric arteries, renal arteries, iliac arteries, arterioles, capillaries and veinlets, and most preferably aorta or carotid.

Effects of this Invention

The features and advantages of this invention will be summarized as follows:

(i) The present invention relates to a composition for dissolving thrombus comprising a peptide comprising Arg-Gly-Asp motif, a pharmaceutical composition for treating stenotic or occlusive vascular diseases which comprises the same, and a thrombus dissolving method and a method for treating stenotic or occlusive vascular diseases comprising administering the same.

(ii) The compositions and methods of the present invention have the advantage that they effectively dissolve already formed thrombus by adopting the principle of targeting integrin within the thrombus such as platelet surface GPIIb-IIIa, which is not the same as the existing principle of plasminogen activation.

(iii) Also, the compositions and methods of the present invention have a nerve-protecting function as they effectively open as far as the microvasculature, without the occurrence of restenosis after penetration.

DETAILED DESCRIPTION

Figure 1A:
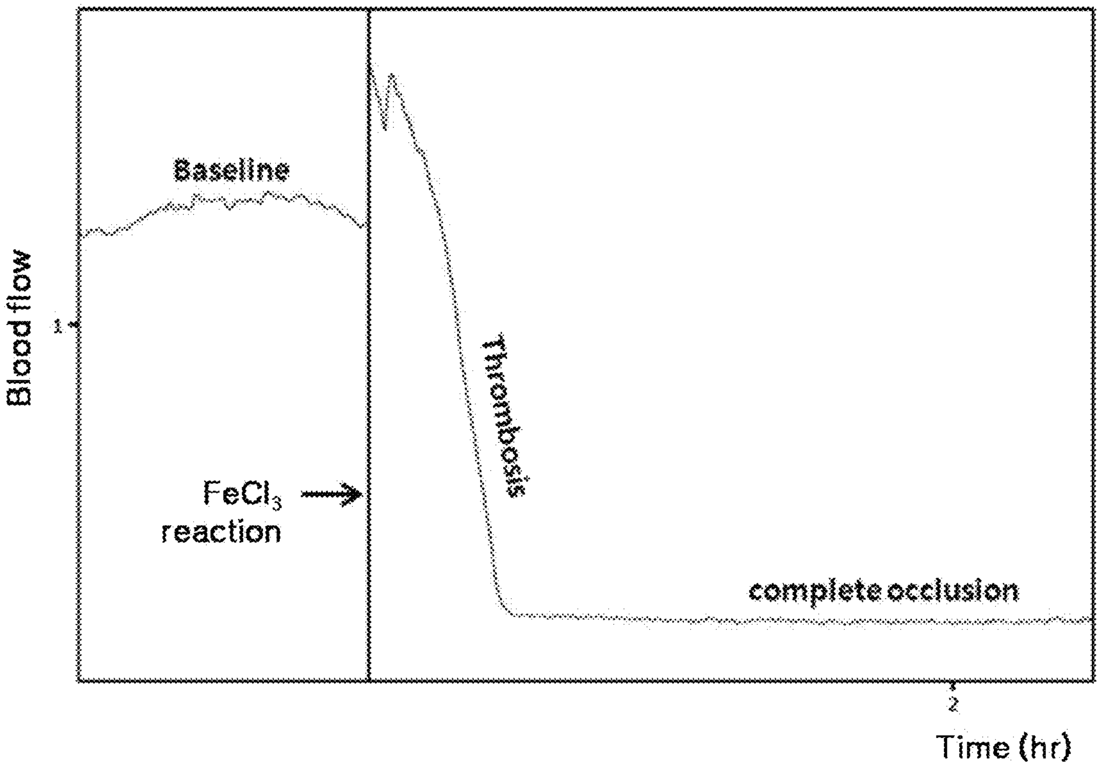
FIG. 1*a* represents the result of occlusion pattern according to $FeCl_3$ application. After $FeCl_3$ application, the blood flow was reduced nearly to zero. Finally the blood vessel is occlusived and maintained.

The present invention will now be described in further detail by examples. It would be obvious to those skilled in the art that these examples are intended to be more concretely illustrative and the scope of the present invention as set forth in the appended claims is not limited to or by the examples.

EXAMPLES

Experimental Methods

Experimental Animals and $FeCl_3$-Induced Carotid Artery Thrombosis 8-week-old male ICR (Institute of Cancer Research) mice (OrientBio) were used. The care and use of laboratory animals were performed according to institutionally approved protocol in accordance with the National Institutes of Health's Guide for the care and use of laboratory animals. For operative procedures, the animals were anesthetized with an inhalation of 5% isoflurane in a mixture of 70% $N_2O$ and 30% $O_2$. Anesthesia was maintained with 2% isoflurane. During the operative procedures, body temperature was monitored continuously with a rectal probe and was maintained at 37.0±0.2° C. by means of a homeothermic blanket control unit and heating pad (Harvard Apparatus, Holliston, Mass.). To test the thrombolytic activity of r-saxatilin in vivo, $FeCl_3$ (Sigma Aldrich, USA)-induced carotid thrombus model was utilized. A midline cervical incision was made, and the left common carotid artery was carefully dissected under a surgical microscope. An ultrasonic Doppler flow probe (Transonic MA0.7PSB) was placed around midportion of the common carotid artery (CCA). Carotid blood flow was obtained with a Transonic TS420 Blood Flow Meter (Transonic Instruments, Ithaca, N.Y.) and iWorx IX-304T data acquisition system (iWorx Systems, Inc., Dover, N.H.). The control baseline flow of the CCA was measured for 5 minutes. After the determination of the control baseline flow, the probe was removed. Oxidative vascular injury with chemical stress was induced by placing a filter paper (700×500 μm) saturated with 50% $FeCl_3$ on the adventitial surface of the midpoint of the exposed CCA for 5 min. After removing the filter paper, the CCA was washed with normal saline and its blood flow was recorded. Thrombus formation and arterial occlusion were determined by decrease of blood flow and the complete occlusion was defined as absence of blood flow maintained for 10 minutes.

Determination of Thrombotic Occlusion and Size Measurement

Consistency of the model in formation and size of the thrombus was assessed. Ten minutes after complete occlusion, the injured CCA segments were excised and immersed in 4% paraformaldehyde for fixation, and embedded in paraffin for histological analysis. The paraffin blocks were consecutively sectioned in a longitudinal direction with 3 μm-thickness. The sectioned slices were mounted on glass slides, and stained with hematoxylin (Dako, Denmark) and eosin (Sigma Aldrich, USA). The size of the thrombus (longitudinal length and area) in each animal was determined by using the Scion Image Analysis software (Scion Co., Frederick, Mass., USA) in a slice that showed the biggest thrombus size.

Recombinant saxatilin used as a thrombolytic agent Saxatilin used as a thrombolytic agent in the present examples was used recombinant saxatilin (r-saxatilin), which is isolated and purified according to the method described in Republic of Korea Patent Publication No. 2002-0064787, and its amino acid sequence is shown as set forth in SEQ ID NO:12.

Intravenous Thrombolysis by Recombinant Saxatilin

Ten minutes after occlusion of the CCA, r-saxatilin was administered intravenously via the left femoral vein by using an infusion pump (KD Scientific Inc., USA) connected to PE-10 tubing. The carotid blood flow was continuously monitored for 2 hours from the initial time of injection.

Dose Response of R-Saxatilin

To evaluate dose response of r-saxatilin, the animals were randomly divided into seven groups (five mice in each group): normal saline (control group), 1, 1.75, 2.5, 3.75, 5.0, and 10.0 mg/kg of r-saxatilin administration groups. 10% of the dose was administered in bolus intravenously and the rest was infused continuously for 60 min.

Administration Methods of R-Saxatilin

Effects of r-saxatilin for thrombolysis were assessed according to administration method. For this experiment, a total dose of 5 mg/kg of r-saxatilin was used in each animal, and the animals were divided into four groups (five mice in each group): (a) bolus injection of total dose (5 mg/kg); (b) double bolus injection of r-saxatilin with a half dose (2.5 mg/kg) of r-saxatilin at 10 min after occlusion and 60 min after the first bolus injection; (c) a half dose bolus injection (2.5 mg/kg) at 10 min after occlusion, and then continuous infusion for 60 min of the remaining dose; and (d) bolus injection of 10% of the total dose (0.5 mg/kg) at 10 min after occlusion, and then continuous infusion of the remaining dose (4.5 mg/kg) for 60 min.

Assessment of Recanalization

The presence and degree of recanalization were assessed by measuring blood flow. Data of blood flow at baseline and those monitored continuously for 2 hours after CCA occlusion were acquired by using iWorx Labscribe2 data acquisition software (version 2.045000). Immediately after 2 hours of blood flow monitoring, the CCA was obtained in all mice, fixed with 4% paraformaldehyde solution, and embedded in paraffin for histological examination. The paraffin blocks were consecutively sectioned in a transverse direction with 3 μm-thickness, mounted on a glass slide, and stained with hematoxylin and eosin.

Dose-Response of R-Saxatilin

The carotid blood flow was analyzed by the area under the flow-time curves. All the measured values were standardized by the minimum blood flow of each animal to avoid differences caused by variation of physiological condition between animals. The thrombolytic effect was calculated as below, and expressed as percent of mean control baseline blood flow: (mean blood flow of r-saxatilin treatment time/mean blood flow of control baseline)×100(%). The mean values of each group in dose response study were calculated and demonstrated by a standard thrombolytic activity curve (mean±SD).

Time-Pattern of Thrombolytic Effects

The average blood flow of every 1 min was calculated in each animal for showing representative time-dependent pattern of respective dose and administration method or r-saxatilin. The mean values of all animals in each group were calculated and the temporal changes were shown as continuous bar graphs (mean±SD).

Time to Recanalization

Time from administration of r-saxatilin to effective recanalization was assessed. Effective recanalization was defined as restoring of the blood flow to at least 50% of the control baseline level, which was maintained longer than 30 min.

Establishment of Expression System of Snake Venom-Derived Saxatilin Derivatives

Cloning of Sequence-Optimized Saxatilin Derivatives and Preparation of pPIC9 Vector

*Pichia* expression system and vector were constructed and used as an expression system of saxatilin derivatives.

First, for preparing peptide sequence-optimized proteins, codon optimization with codon usage frequency was undertaken for expression of the saxatilin gene in *Pichia* host cells, thereby converting the saxatilin gene to the optimized nucleotide sequence (SEQ ID NO:1 to SEQ ID NO:21). The optimized nucleotide sequence was designed to clone into a pPIC9 vector (Invitrogen) suitable for expression in *Pichia* host cells (GS115, $His^-$; EyeGene Inc.). More specifically, XhoI restriction site was positioned at 5'-portion of the saxatilin gene and EcoRI restriction site at its 3'-portion. The gene was inserted between XhoI and EcoRI restriction sites positioned in MCS (multicloning site) of pPIC9 vector as vector for *Pichia* host cell (GS115) expression. The saxatilin gene cloned into pPIC9 vector was prepared to express the fusion protein form with yeast α-factor. Where the yeast α-factor was extracellularly secreted by acting as a signal sequence for extracellular secretion of protein, the yeast α-factor was cleaved and removed. Since the synthesized saxatilin was secreted into medium, the medium was collected and purified to use as saxatilin sample for effective activity analysis.

Bacteria Strain Preparation for Preserving Saxatilin Derivatives Expression Vector For isolation/purification and preservation of expression vector, DH5a was transformed to prepare bacteria strain for preservation (Glycerol stock, storage at −70° C.). For transformation of *Pichia pastoris*, a lots of expression vectors were used in the transformation process of *Pichia* host cell (GS115), as compared with transformation of DH5a. In order to induce site specific recombination as chromosome insertion process of saxatilin gene, plasmid was linearized through cleavage of specific gene potion (HIS4 locus) in expression vector (i.e., in case of pPIC9 vector, SalI or StuI was used to cleave). GS115 competent cell were mixed with 10-50 μg of linearized expression vector plasmid and 40 μg of carrier DNA (salmon sperm DNA) to transform. Then, well-grown single colony was selected. Genome DNA was extracted and conducted to PCT to verify whether Saxatilin gene introduced into cell by transformation was inserted between his4 gene on *Pichia* (GS115) chromosome.

Expression Verification of Saxatilin Derivatives

Parts of *Pichia* strain verified insertion of gene were selected to determine expression of protein. Candidate strain was cultured and analyzed by SDS-PAGE method.

Expression and Purification of Saxatilin Derivatives

Saxatilin Derivatives Sample Preparation for Effective Activity Analysis

In order to prepare saxatilin derivatives protein sample, the selected strain was massively cultured in flask. The culture condition was same as the strain culture condition except for increasing methanol input and oxygen used in metabolism. Briefly, fermentation used the strain was conducted at 30° C. using fermenter Fed-batch (KF7; KBT Co., Ltd.). The fermenter system was 7 liter (actually 5 liter), control system was temperature/rpm/Air/O2/pH/DO, and operation mode was Batch & Fed-batch, Semi-continuous. First, the strain was cultured in YNB medium (Yeast Nitrogen Base 1.7 g, ammonium sulfate 5.0 g, potassium phosphate (monobasic) 11.5 g, potassium phosphate (dibasic) 2.85 g, glycerol per 1 liter) for 1 day, the resulting medium was cultured with batch culture (pH 5.0; start-up Medium, phosphoric acid 54 ml, calcium sulfate (anhydrous) 1.8 g, potassium sulfate 36 g, magnesium sulfate ($7H_2O$) 30 g, potassium hydroxide 8.26 g, glycerol 80 g, TMS (Trace metal solution) 8.8 ml per 2 liters) for 1 day. The TMS solution (storage at room temperature) was prepared that $CuSO_4$-$5H_2O$ 6.0 g, $MnSO_4$-$5H_2O$ 4.28 g, $ZnCl_2$ 20.0 g, $FeSO_4$-$7H_2O$ 65.0 g, $H_2SO_4$ 5 ml, NaI 0.08 g, $Na_2MoO_4$-$2H_2O$ 0.2 g, Boric acid 0.02 g, $CoCl_2$-$6H_2O$ 0.92 g, and Biotin 0.2 g were sequentially added to suitable amount of distilled water to dissolve, adjusted to 1 liter of volume and sterilized by 0.2 μm filter. The batch medium was conducted to Glycerol Fed-batch culture (GFBM, pH 5.0; 0.5 liter of glycerol was mixed with 0.5 liter of distilled water, steam-sterilized, cooled to room temperature and added to 12 ml of TMS per GFBM 1 liter to prepare) for 8-10 hours. The medium was treated with methanol (MeOH) for 3 hours to induce protein, and then conducted to MeOH Fed-batch culture (MFBM, pH 5.0; 12 ml of TMS per 99.9% industrial MeOH 1 liter was mixed to prepare, it was immediately used without any extra sterilization treatment, and containers and pipes were steam-sterilized to use) for 3 days. The culture was conducted to MeOH semi-continuous as necessary. At this time, MeOH feed rate was 6-15 ml/liter/hr at 1 day and 15-20 ml/liter/hr at 2-3 day using DO-STAT(DO set pt., min. 6 ppm). Meanwhile, oxygen was provided since GFBM culture and pure oxygen supply was 0.2-0.4 vvm.

Protocols for Isolation and Purification of Saxatilin Derivatives

Isolation and purification of saxatilin derivatives (SX1, SX2, SX3, XL1, XL2, XL3, LS1, LS2 and LS3) were conducted as follows.

First, yeast strain transformed saxatilin derivatives was high density-cultured and then, fermentation supernatant was collected. For resin absorption, the supernatant was pretreated with ammonium sulfate (A/S) to 2 M of concentration and conducted to Capturing chromatography. Phenyl sepharose 6 FF resin was packed to 75 ml of Phenyl Sepharose FF column (GE Healthcare) and the supernatant was loaded. According to scale-up protocol, fermentation supernatant was absorbed, washed with 5 times of column volume (5 CV) of equiponderation buffer solution (2.0 M A/S in PBS) and 4 times of column volume (4 CV) of washing buffer solution, and eluted active pool with concentration of 1.0 M, 0.8 M, 0.7 M and 0.5 M A/S. As a result, elution buffer solution of ‘x0.5 PBS buffer solution+0.8 M A/S’ has the best elution results in terms of quality and yield. Regeneration of column was conducted with 3 times of column volume (3 CV) of 1 N NaOH and 5 times of column volume (5 CV) of distilled water.

Second, abrasive chromatography was conducted using the obtained elution buffer solution. After pre-treatment of the same condition as described above, resin was packed to 215 ml of SOURCE30 RPC/FINELINE Pilot35 column (GE Healthcare) and the elution buffer solution was loaded to absorb. After washing with 5 times of column volume (5 CV) of equiponderation buffer solution (0.1% TFA in DDW) and 5 times of column volume (5 CV) of washing buffer solution (0.1% TFA in 10% Acetonitrile(ACN)), active pool was eluted with 3 times of column volume (3 CV) of elution buffer solution (0.1% TFA in 30% ACN). Afterwards, regeneration of column was conducted with 3 times of column volume (3 CV) of 1 N NaOH (in 40% ACN).

Third, Sephadex LH20 chromatography (GE Healthcare) was conducted. Active pool obtained from RPC was exchanged with final storage buffer solution to apply to purification product. MWCO 5 KDa UF was used for this. Since saxatilin molecular weight is 7.7 kDa, it was expected to decrease of the yield. The final result also showed more than 10% of decrease. Particularly, since organic solvent acetonitrile was included approximately 30% in RPC active pool, UF membrane was used. Meanwhile, instead of UF method, Gel Filtration may be used. Sephadex LH20 is resin which can be used organic solvent and very suited for desalination of saxatilin, thereby final saxatilin derivatives were obtained.

The obtained saxatilin derivatives were sterilized by 0.2 μm filter and measured purity. Then, high purity saxatilin derivatives were freeze-dried, sterile-packed and stored at −80° C. until administration.

Afterwards, intravenous thrombolysis and dose response by saxatilin derivatives were conducted with the same method of recombinant saxatilin as described above (FIGS. 7 and 8).

Results

The Consistency of an Animal Model

Figure 1B:
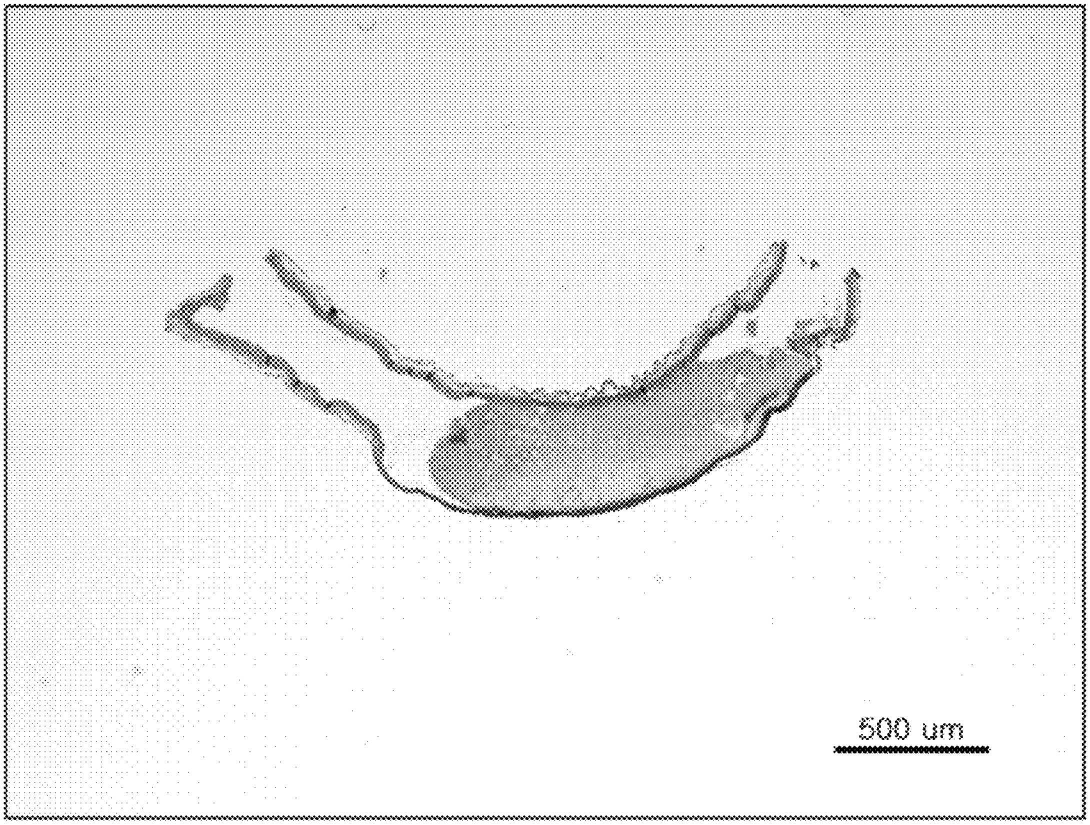
FIG. 1*b* represents the result of H&E staining for detecting the thrombus. As a result of measuring the size of the thrombus generated in 5 animals, the uniform size of the thrombus is generated such that it was considered as a suitable model to verify the effect by thrombolytic agent.
Figure 2:
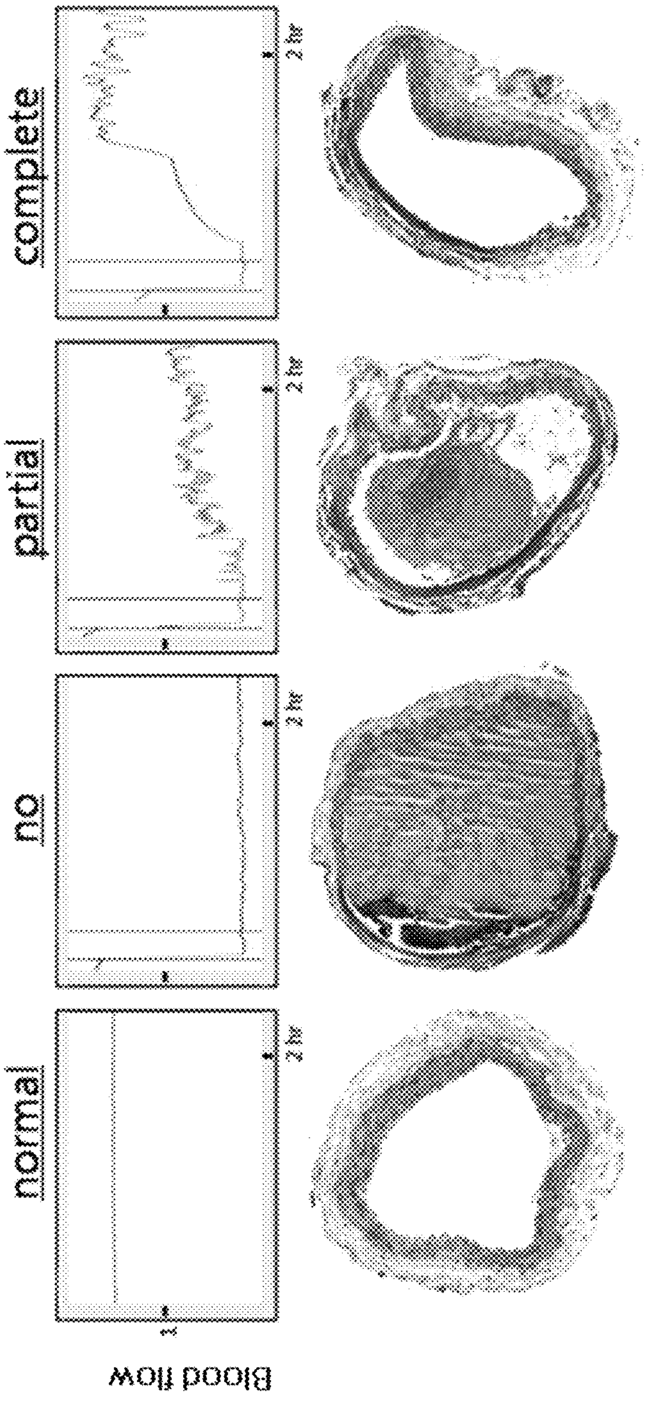
FIG. 2 represents the results of measurement of the blood flow in normal blood vessel and various occlusion blood vessels and detection of thrombus generated in the vessels thereof.

After 5 min of $FeCl_3$ application, the blood flow of the CCA was rapidly and consistently reduced nearly to zero in all 5 animals examined (FIG. 1*a*). The thrombotic occlusion of the CCA was demonstrated on histologic examinations in them (FIG. 1*b*). Sizes of the thrombus were similar between the animals (length: 1.139±0.091 mm, area: 0.799±0.139 $mm^2$). In the r-saxatilin treated groups, histologic examinations showed that the thrombus was not seen in the carotid lumen of mice with completely restored carotid blood flow, whereas the thrombus was remained in the carotid lumen of mice without carotid blood flow restored or partially restored blood flow (FIG. 2).

Dose-Dependent Thrombolytic Effects of R-Saxatilin

Figure 3:
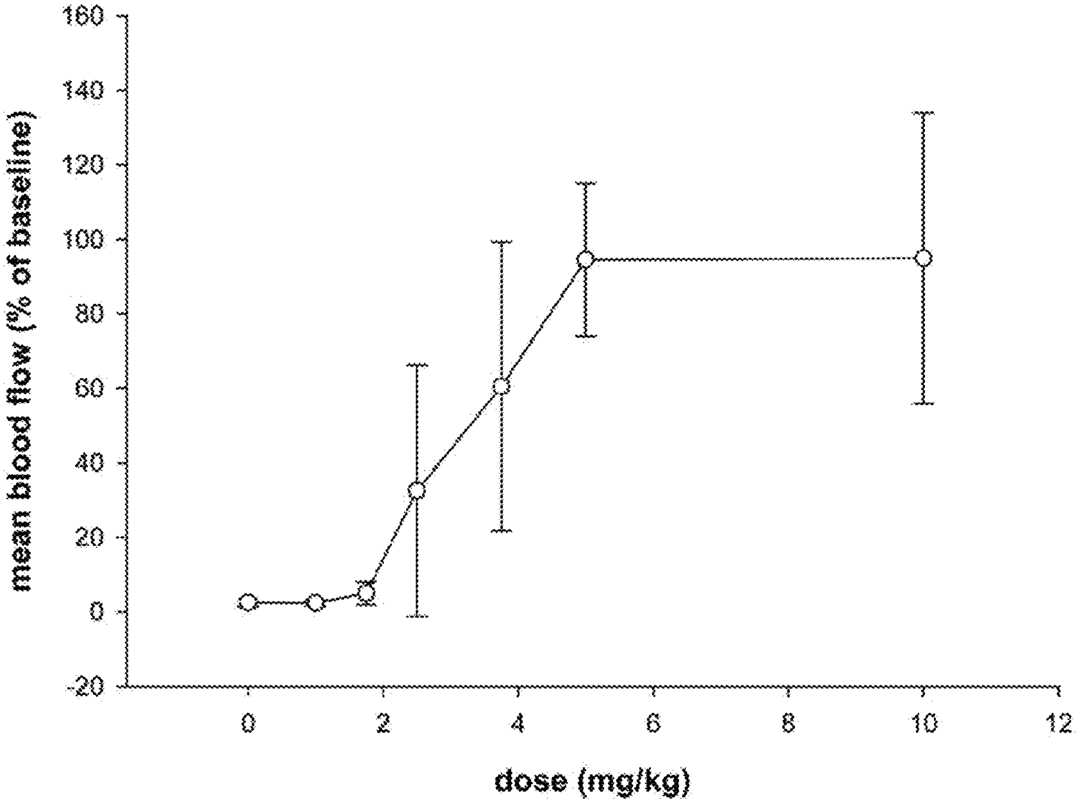
FIG. 3 represents the graph measuring changes in the blood flow according to the dose of r-saxatilin. As doses of r-saxatilin increase, the blood flow (the area under the flow-time curves) was restored nearly to the baseline level (r-saxatilin doses of 5 mg/kg and 10 mg/kg).

Dose-dependent effects of r-saxatilin were determined using data of area under the flow-time curve (FIG. 3). r-saxatilin treatment did not cause any notable change either at a dose of 1 mg/kg (2.36±0.78%) or 1.75 mg/kg (4.97±3.94%), when comparing with normal saline group (2.47±1.07%). Restoring blood flow was observed at a dose of 2.5 mg/kg (32.50±33.70%) and increased in a dose-dependent manner. The blood flow was restored nearly to the baseline level (94.50±20.47%) at a dose of 5 mg/kg. There was no significant difference between 5 and 10 mg/kg of r-saxatilin.

Effects of R-Saxatilin by Administration Methods

The optimal administration method of intravenous r-saxatilin administration was determined by using a total dose of 5 mg/kg, which showed satisfactory effects in the dose-response study. The mean percentages of the blood flow, which were compared to the baseline blood flow were as follows: (a) 77.01±46.11% in the group with a bolus injection of a total dose; (b) 85.23±29.95% in the group with double bolus injection with a half dose; (c) 80.72±30.13% in the group with a half dose bolus injection; and (d) continuous infusion of the remaining dose, and 94.50±20.47% in the group with a bolus injection of 10% of the total dose and continuous infusion of the remaining dose.

Figure 4:
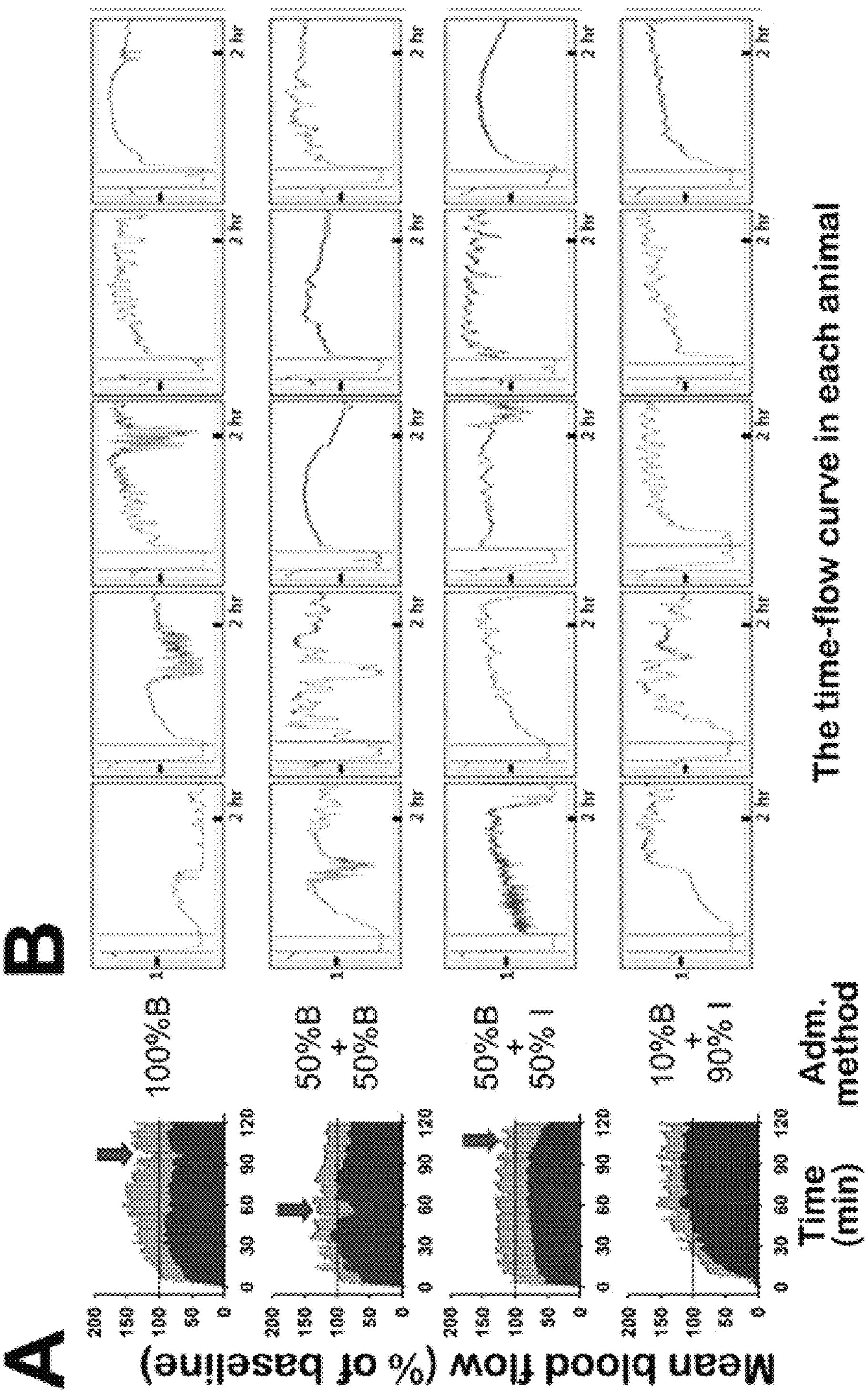
FIG. 4 represents the comparison results of thrombolytic effect of saxatilin according to administration method. Blue arrow in panel A indicates the time point of reocclusion observed. B in panel A indicates bolus injection. I in panel A indicates continuous intravenous infusion.

Decrease of the thrombolytic effects was observed at different time points according to the administration method. Abrupt reocclusion was observed at time points as follows: (a) about 50 min after the first injection in mice treated with double bolus injection; (b) about 100 min after a bolus injection of total dose; and (c) about 110 min after a half dose bolus injection and following continuous infusion of the other half dose (FIG. 4). There was no reocclusion observed with bolus injection of 10% of the total dose and continuous infusion of the remaining dose.

Time to Recanalization by R-Saxatilin

No effective recanalization was observed in mice treated with normal saline, r-saxatilin of 1 mg/kg or r-saxatilin of 1.75 mg/kg. Only two of five mice treated with 2.5 mg/kg and three of five mice treated with 3.75 mg/kg of r-saxatilin achieved effective recanalization.

Figure 5:
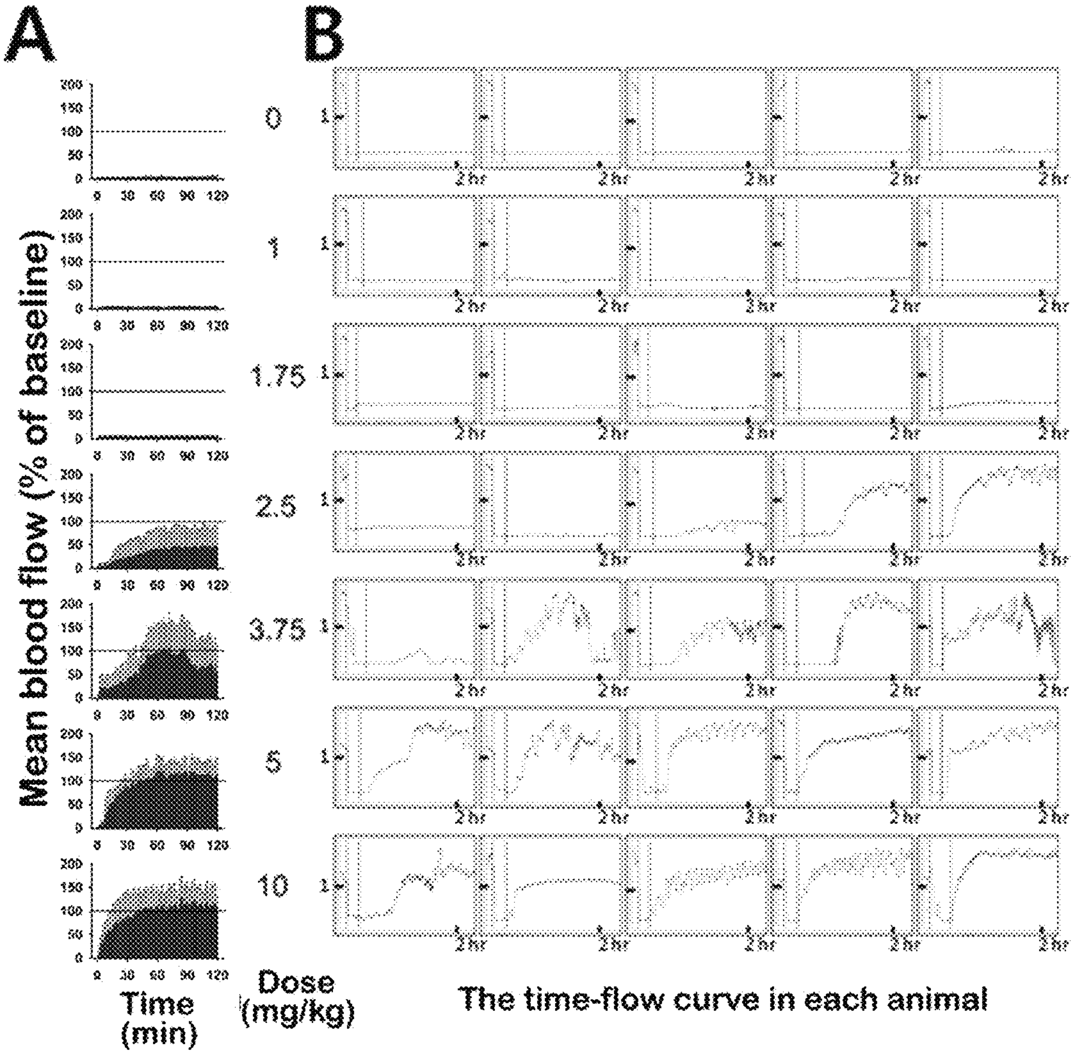
FIG. 5 represents the results of saxatilin dose-dependent thrombolytic effect. Various concentrations of saxatilin were administrated to $FeCl_3$-induced animal and the blood flow was continuously monitored for 2 hours.

Effective recanalization was defined as restoring blood flow to the 50% of the baseline level and maintained longer than 30 min (FIG. 5). It was observed in all mice treated with r-saxatilin at a dose of 5 or 10 mg/kg (FIG. 5). Time to effective recanalization was as follows: (a) 32.92±23.52 min in mice treated with r-saxatilin at 2.5 mg/kg; (b) 21.75±21.62 min in mice treated with r-saxatilin at 3.75 mg/kg; (c) 13.92±6.02 min in mice treated with r-saxatilin at 5 mg/kg; and (d) 19.46±19.75 min in mice treated with r-saxatilin at 10 mg/kg. Also, effective recanalization was evaluated according to administration method of r-saxatilin. All mice treated 5 mg/kg of r-saxatilin achieved effective recanalization except two mice administered with bolus injection of total dose. Time to effective recanalization was as follows: (a) 2.86±0.22 min in mice treated with a bolus injection of total dose; (b) 13.44±26.31 min in mice treated with double bolus injection; (c) 19.48±25.94 min in mice treated with a half dose bolus injection and following continuous infusion of the other half dose; and (d) 13.92±6.02 with bolus injection of 10% of the total dose and continuous infusion of the remaining dose. Time to effective recanalization was shorter in the group with bolus injection of total dose than the group with bolus injection of 10% of the total dose and continuous infusion of the remaining dose (p=0.004).

Mortality and Bleeding after the R-Saxatilin Treatment

Total 51 animals were used for evaluation of thrombolytic effects of r-saxatilin. Among them, one animal was died from bleeding in the cervical incision site about 90 min after the bolus injection in the 5 mg/kg of r-saxatilin bolus injection group. Additionally, in the same group, one animal suffered bleeding in the cervical incision by 5 mg/kg of r-saxatilin bolus injection.

Activity Measurement of Saxatilin Derivatives

In Vitro Platelet Aggregation Assay

Saxatilin derivatives and ADP were administrated to mouse PRP (platelet rich plasma) and measured aggregation level using Aggregometer (CHRONO-LOG, USA) to evaluate activity of the present saxatilin derivatives (Table 1).

TABLE 1

In vitro activity of r-saxatilin and saxatilin derivatives

| Inhibitor | $IC_{50}$(nM) |
|---|---|
| saxatilin | 176 |
| SX1 | 349 |
| SX2 | 991 |
| SX3 | 918 |
| XL1 | 1,007 |
| XL2 | 986 |
| XL3 | 1,064 |
| LS1 | 1,117 |
| LS2 | 1,009 |
| LS3 | 1,003 |

Figure 6:
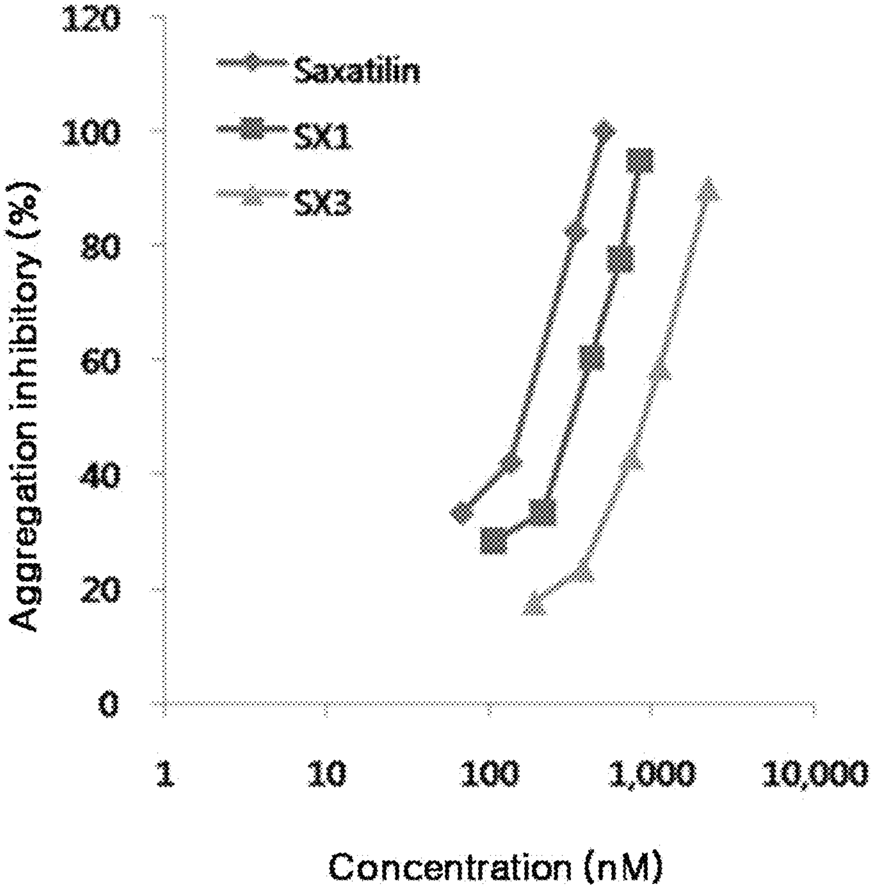
FIG. 6 represents the results of platelet aggregation inhibitory level of saxatilin and saxatilin derivatives (SX1 and SX3).

As shown in Table 1 and FIG. 6, activities of SX1 (349) and SX3 (918) as saxatilin derivatives of the present invent were the highest activity and it could be verified that the platelet aggregation inhibitory pattern is similar to saxatilin.

Taken together, although there are some differences between all saxatilins and saxatilin derivatives, where levels of aggregation inhibition according to the range of treatment concentration were compared, it could be determined that the present saxatilin derivatives treatment (for example, SX1, 1 μM; SX3, 4 μM) is similar to the effect of saxatilin (approximately 0.7 μM) (FIG. 6).

Thrombolytic Effects of Saxatilin Derivatives

Figure 7:
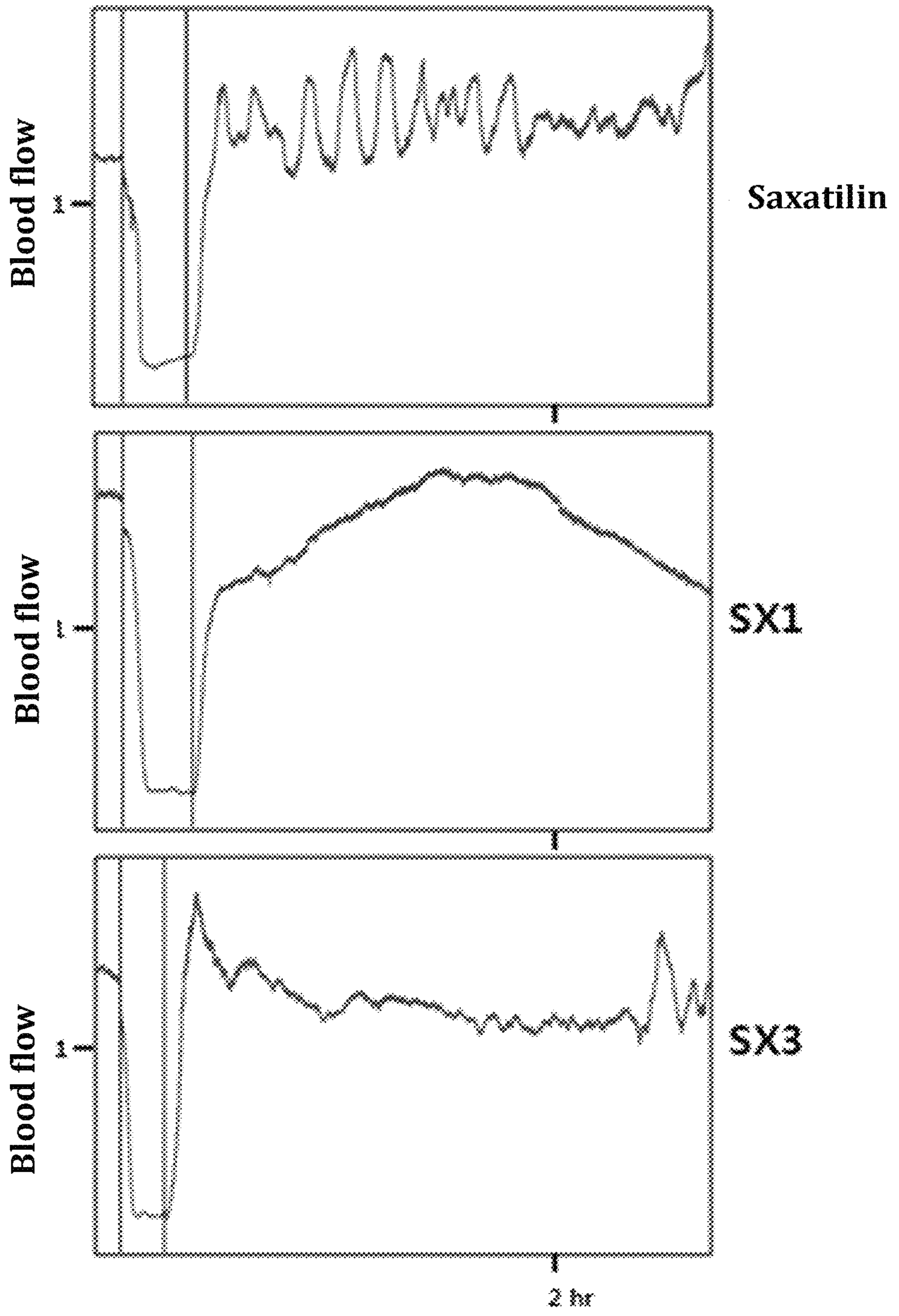
FIG. 7 represents the results of changes in the blood flow through treatments of saxatilin and saxatilin derivatives (SX1 and SX3) in 40 mg/kg of dose.
Figure 8:
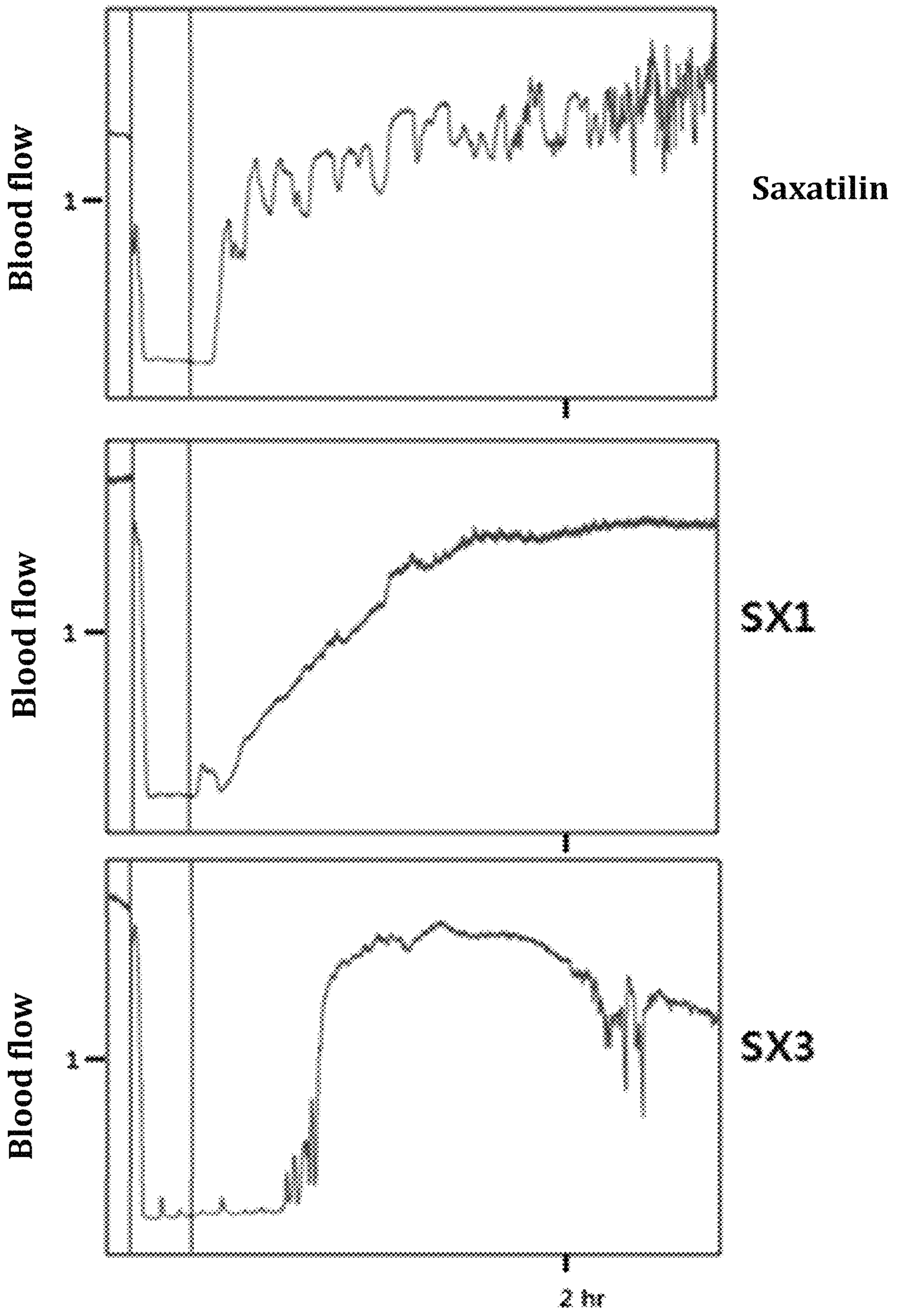
FIG. 8 represents the results of changes in the blood flow through treatments of saxatilin and saxatilin derivatives (SX1 and SX3) in 20 mg/kg of dose.

Thrombolytic effects of saxatilin and saxatilin derivatives (SX1, SX3) were evaluated using data of the area under the flow-time curve as the same experiments (FIGS. 7 and 8). Administration doses of saxatilin and saxatilin derivatives were equally treated. Where 20 mg/kg of dose was administrated, saxatilin-administrated group was restored 60.92±39.52% of blood flow, SX1-administrated group was restored 78.56±16.24% of blood flow, and SX3-administrated group was restored 69.15±14.89% of blood flow. Where 40 mg/kg of dose was administrated, both of saxatilin-administrated group and saxatilin derivatives-administrated group (SX1, SX3) were restored to normal blood flow and maintained without reocclusion. Even although there was no reocclusion, saxatilin derivatives-administrated groups (SX1, SX3) were analyzed to show the blood flow fluctuation less than the wild type saxatilin, demonstrating that the blood flow was stably maintained (FIG. 7).

At 20 mg/kg dose, there are no significant differences in restored levels of the blood flow. However, post-recanalization reocclusion frequency and the blood flow fluctuation were significantly reduced in thrombolytic treatment by saxatilin derivatives (SX1) compared with the wild type saxatilin, addressing that the normal blood flow was stably maintained (FIG. 8).

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES (1995). "Tissue plasminogen activator for acute ischemic stroke. The National Institute of Neurological Disorders and Stroke rt-PA Stroke Study Group." N Engl J Med 333(24): 1581-1587.

Abou-Chebl, A., C. T. Bajzer, et al. (2005). "Multimodal therapy for the treatment of severe ischemic stroke combining GPIIb/IIIa antagonists and angioplasty after failure of thrombolysis." Stroke 36(10): 2286-2288.

Abumiya, T., R. Fitridge, et al. (2000). "Integrin alpha(IIb) beta(3) inhibitor preserves microvascular patency in experimental acute focal cerebral ischemia." Stroke 31(6): 1402-1409; discussion 1409-1410.

Adams, H., R. Adams, et al. (2005). "Guidelines for the early management of patients with ischemic stroke: 2005 guidelines update a scientific statement from the Stroke Council of the American Heart Association/American Stroke Association." Stroke 36(4): 916-923.

Adams, H. P., Jr., M. B. Effron, et al. (2008). "Emergency administration of abciximab for treatment of patients with acute ischemic stroke: results of an international phase III trial:

Abciximab in Emergency Treatment of Stroke Trial (AbESTT-II)." Stroke 39(1): 87-99.

Alexandrov, A. V. and J. C. Grotta (2002). "Arterial reocclusion in stroke patients treated with intravenous tissue plasminogen activator." Neurology 59(6): 862-867.

Caplan, L. R., J. P. Mohr, et al. (1997). "Should thrombolytic therapy be the first-line treatment for acute ischemic stroke? Thrombolysis—not a panacea for ischemic stroke." N Engl J Med 337(18): 1309-1310; discussion 1313.

Chen, H., W. Mo, et al. (2007). "Characterization of a novel bifunctional mutant of staphylokinase with platelet-targeted thrombolysis and antiplatelet aggregation activities." BMC Mol Biol 8: 88.

Chen, Z. L. and S. Strickland (1997). "Neuronal death in the hippocampus is promoted by plasmin-catalyzed degradation of laminin." Cell 91(7): 917-925.

Choi, J. H., B. T. Bateman, et al. (2006). "Endovascular recanalization therapy in acute ischemic stroke." Stroke 37(2): 419-424.

Choudhri, T. F., B. L. Hoh, et al. (1998). "Reduced microvascular thrombosis and improved outcome in acute murine stroke by inhibiting GP IIb/IIIa receptor-mediated platelet aggregation." J Clin Invest 102(7): 1301-1310.

Ciccone, A., I. Abraha, et al. (2007). "Glycoprotein IIb-IIIc Inhibitors for Acute Ischemic Stroke." Stroke.

Eckert, B., C. Koch, et al. (2005). "Aggressive therapy with intravenous abciximab and intra-arterial rtPA and additional PTA/stenting improves clinical outcome in acute vertebrobasilar occlusion: combined local fibrinolysis and intravenous abciximab in acute vertebrobasilar stroke treatment (FAST): results of a multicenter study." Stroke 36(6): 1160-1165.

Hallenbeck, J. M. and A. J. Dutka (1990). "Background review and current concepts of reperfusion injury." Arch Neurol 47(11): 1245-1254.

Heo, J. H., K. Y. Lee, et al. (2003). "Immediate reocclusion following a successful thrombolysis in acute stroke: a pilot study." Neurology 60(10): 1684-1687.

Hong, S. Y., Y. S. Koh, et al. (2002). "Snake venom disintegrin, saxatilin, inhibits platelet aggregation, human umbilical vein endothelial cell proliferation, and smooth muscle cell migration." Thromb Res 105(1): 79-86.

Hong, S. Y., Y. D. Sohn, et al. (2002). "Structural and functional significance of disulfide bonds in saxatilin, a 7.7 kDa disintegrin." Biochem Biophys Res Commun 293(1): 530-536.

Hussain, M. S., R. Lin, et al. (2010). "Symptomatic delayed reocclusion after initial successful revascularization in acute ischemic stroke." J Stroke Cerebrovasc Dis 19(1): 36-39.

Jang, Y. J., 0. H. Jeon, et al. (2007). "Saxatilin, a snake venom disintegrin, regulates platelet activation associated with human vascular endothelial cell migration and invasion." J Vasc Res 44(2): 129-137.

Konstantinides, S., K. Schafer, et al. (2001). "Plasminogen activator inhibitor-1 and its cofactor vitronectin stabilize arterial thrombi after vascular injury in mice." Circulation 103(4): 576-583.

Kurz, K. D., B. W. Main, et al. (1990). "Rat model of arterial thrombosis induced by ferric chloride." Thromb Res 60(4): 269-280.

Lopez-Yunez, A. M., A. Bruno, et al. (2001). "Protocol violations in community-based rTPA stroke treatment are associated with symptomatic intracerebral hemorrhage." Stroke 32(1): 12-16.

Matys, T. and S. Strickland (2003). "Tissue plasminogen activator and NMDA receptor cleavage." Nat Med 9(4): 371-372; author reply 372-373.

Nicole, O., F. Docagne, et al. (2001). "The proteolytic activity of tissue-plasminogen activator enhances NMDA receptor-mediated signaling." Nat Med 7(1): 59-64.

Phillips, D. R., I. F. Charo, et al. (1988). "The platelet membrane glycoprotein IIb-IIIc complex." Blood 71(4): 831-843.

Qureshi, A. I., A. M. Siddiqui, et al. (2004). "Reocclusion of recanalized arteries during intra-arterial thrombolysis for acute ischemic stroke." AJNR Am J Neuroradiol 25(2): 322-328.

Rha, J. H. and J. L. Saver (2007). "The impact of recanalization on ischemic stroke outcome: a meta-analysis." Stroke 38(3): 967-973.

Seitz, R. J., M. Hamzavi, et al. (2003). "Thrombolysis with recombinant tissue plasminogen activator and tirofiban in stroke: preliminary observations." Stroke 34(8): 1932-1935.

Seitz, R. J., S. Meisel, et al. (2004). "The effect of combined thrombolysis with rtPA and tirofiban on ischemic brain lesions." Neurology 62(11): 2110-2112.

Shattil, S. J. and M. H. Ginsberg (1997). "Integrin signaling in vascular biology." J Clin Invest 100(11 Suppl): S91-95.

Sohn, Y. D., S. Y. Hong, et al. (2008). "Acute and repeated dose toxicity studies of recombinant saxatilin, a disintegrin from the Korean snake (Gloydius saxatilis)." Toxicon 51(3): 406-417.

Wang, Y. F., S. E. Tsirka, et al. (1998). "Tissue plasminogen activator (tPA) increases neuronal damage after focal cerebral ischemia in wild-type and tPA-deficient mice." Nat Med 4(2): 228-231.

Wardlaw, J. M., V. Murray, et al. (2009). "Thrombolysis for acute ischaemic stroke." Cochrane Database Syst Rev(4): CD000213.

Yepes, M., M. Sandkvist, et al. (2002). "Regulation of seizure spreading by neuroserpin and tissue-type plasminogen activator is plasminogen-independent." J Clin Invest 109(12): 1571-1578.

What is claimed is:

1. A method for thrombolysis in a patient with ischemic stroke in need thereof, comprising:

administering to a blood vessel of the patient a peptide comprising the amino acid sequence of SEQ ID NO:12 in an amount of 5 to 70 mg/kg/day, wherein a blood vessel of the patient which supplies blood to the brain has become occluded by a thrombus before the administration of the peptide, thereby dissolving the thrombus in the blood vessel, and wherein the method does not include administration of a peptide before thrombus formation.

2. The method according to claim 1, wherein the peptide has disintegrin activity.

3. The method according to claim 1, wherein the peptide is saxatilin.

* * * * *